(12) United States Patent
Wilson

(10) Patent No.: US 7,306,615 B2
(45) Date of Patent: Dec. 11, 2007

(54) ANATOMICAL HANDLE FOR SURGICAL PRECISION SCALPEL

(75) Inventor: Mark P. Wilson, Sarasota, FL (US)

(73) Assignee: Medideas, Inc., Sarasota, FL (US)

(*) Notice: Subject to any disclaimer, the term of this patent is extended or adjusted under 35 U.S.C. 154(b) by 825 days.

(21) Appl. No.: 10/451,019

(22) PCT Filed: Dec. 19, 2001

(86) PCT No.: PCT/IB01/02595

§ 371 (c)(1),
(2), (4) Date: Oct. 23, 2003

(87) PCT Pub. No.: WO02/49520

PCT Pub. Date: Jun. 27, 2002

(65) Prior Publication Data

US 2004/0097999 A1   May 20, 2004

(30) Foreign Application Priority Data

Dec. 20, 2000   (IT) .................... FI2000A0255

(51) Int. Cl.
A61B 17/32   (2006.01)

(52) U.S. Cl. .................... 606/167; 30/2; 30/151

(58) Field of Classification Search ............... 606/132, 606/166, 167; 30/2, 151, 162
See application file for complete search history.

(56) References Cited

U.S. PATENT DOCUMENTS

| 3,748,736 A | 7/1973 | Eisen |
| 5,100,391 A | 3/1992 | Schutte et al. |
| 5,391,169 A * | 2/1995 | McGuire .................... 606/79 |
| 5,730,751 A | 3/1998 | Mobbs et al. |
| 5,887,250 A * | 3/1999 | Shah .................... 455/411 |

FOREIGN PATENT DOCUMENTS

DE   27 31 470 A   1/1978

* cited by examiner

Primary Examiner—Michael J. Hayes
Assistant Examiner—Victor X. Nguyen
(74) Attorney, Agent, or Firm—Egbert Law Offices

(57) ABSTRACT

An anatomic handle for surgical precision scalpel includes a first upper curved body anatomically corresponding to the curved direction of the forefinger, a second underlying body prolonging the first one, having an asymmetrical overturned-saddle shape, a central are area determined by the combination of the first upper body and the second underlying body, two equal and opposite heads to the two terminal parts of the first curved body constituting on the upper part an ergonomic handle, said heads presenting each on the lateral side the joint for an interchangeable blade. The peculiarity of the handle is that its morphological characteristics allow several different grips according to the peculiar surgical situation in which the scalpel is used.

20 Claims, 2 Drawing Sheets

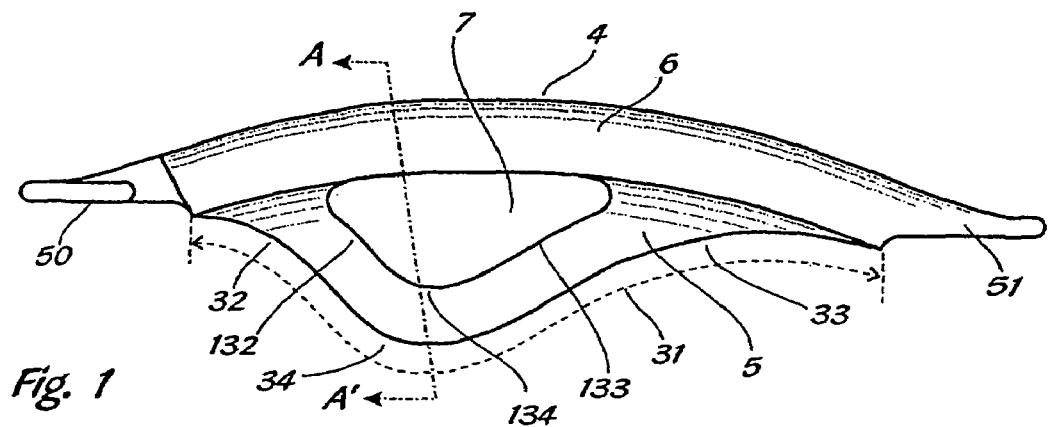
Fig. 1
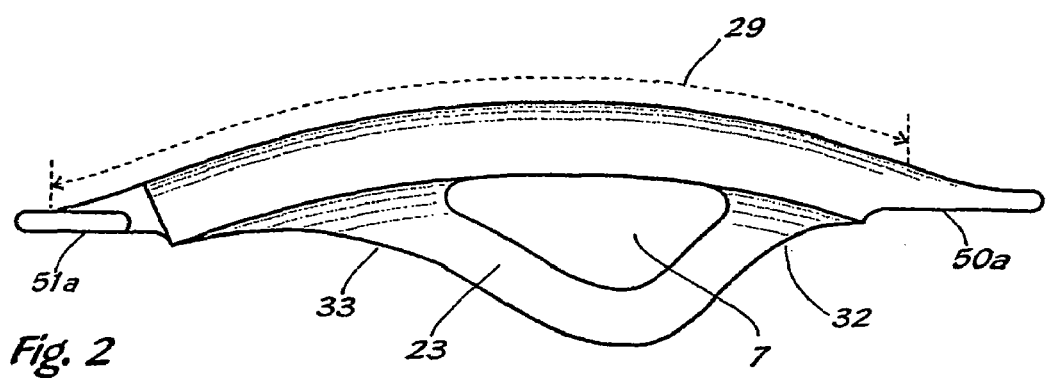
Fig. 2
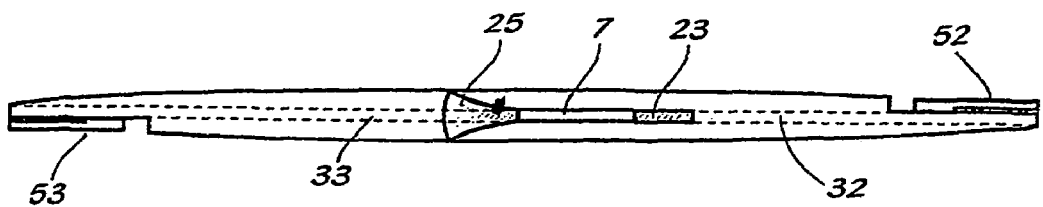
Fig. 3
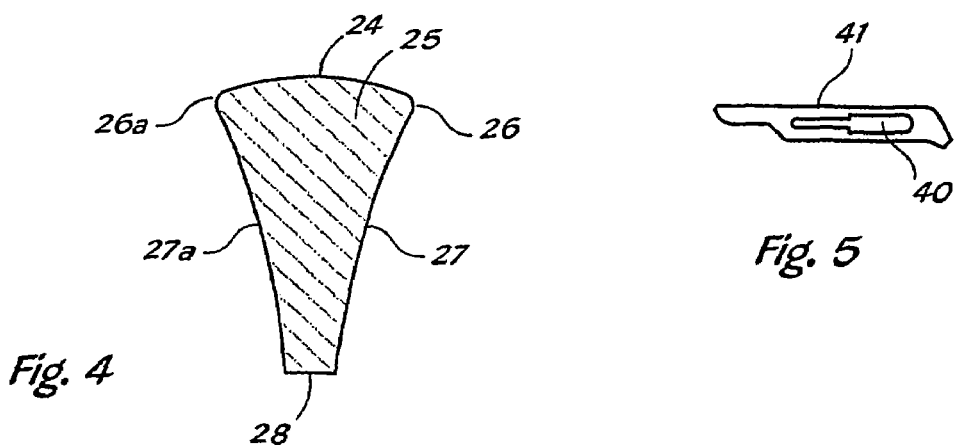
Fig. 4
Fig. 5

ANATOMICAL HANDLE FOR SURGICAL PRECISION SCALPEL

RELATED U.S. APPLICATIONS

Not applicable

STATEMENT REGARDING FEDERALLY SPONSORED RESEARCH OR DEVELOPMENT

Not applicable

REFERENCE TO MICROFICHE APPENDIX

Not applicable

FIELD OF THE INVENTION

The present invention relates to the field of surgical instruments, more specifically a scalpel, indispensable for fundamental maneuvers such as the incision and the dissection in surgical operations on a human body and on an animal's body.

BACKGROUND OF THE INVENTION

The known scalpel, completely carried out in metal and ideally constituted by a first portion acting as an handle and by a second portion constituting the blade, are the preferred surgical instruments for the incision of superficial and deep tissues. The use of scalpel having "a fixed blade" of traditional type is limited, especially because of problems due to its sterilization, to some special operations; the method of disinfection through steam causes the inconvenience to damage the sharpening of the blade, therefore the instrument has to be bathed in suitable disinfectant solutions that protect it from oxidizing actions, or through more advanced methods such as the gamma ray sterilization. The cutting portion, that is the blade, can have different shapes, such as straight, bulged or convex, or be button-shaped, crescent-shaped or have two cutting edges; as the handle is generally constituted by a rectilinear, flat bar, the specific shape of the blade is relevant because it has to be suitable to the specific incision or scission of the tissues and to the operating technique that the surgeon intends to adopt. These necessities have brought about the use of scalpel having interchangeable blades and to combine the suitable blades each time, so that only the handle has to be sterilized through conventional methods which are usually used also for other usual surgical instruments; moreover, blades are supplied by several manufacturing companies in pre-sterilized wrappings.

Many kind of handles are required to cover the range of the several operating techniques used; they have different length and shape, on which the differently shaped blades have to be applied.

As regards to conventional handles, constituted by a bar having a longitudinally rectilinear variable section, the grasping area is generally placed towards the blade and provided on the two faces with transversal notches or readings having the purpose of achieving a stable grip, whereas the balancing of the instrument is provided by means of a rear flat tang having a larger size than the opposite terminal part; to help the operating movements on the fleshy parts and in interosseous spaces, the head which holds the blade can be also variously angled, such as in the case of the scalpel known as "Collin" whose handle is greatly flat and has a double size compared to the usual scalpel, with the tang much rounded and allowing the grip between the thumb and the forefinger.

It is further known a double handle having interchangeable blades which can be inserted on the opposite heads, which can have two contiguous gripping areas, having different surface and which allow the use of two complementary blades necessary for specific surgical techniques.

U.S. Pat. No. 5,571,127 (DECAMPLI) discloses a scalpel handle having the physical and ergonomic features of a conventional surgical scalpel handle, but which houses a retractable blade support fit for engaging scalpel blades having standard assembling housings. The scalpel blade is extended and retracted by the surgeon's forefinger as a natural part of the supporting and guiding movement of the scalpel handle, and it is characterized by the fact to have few movable parts being therefore easily disassembled and sterilized. Moreover, methods are provided for replacing scalpel blades that are essentially the same used for conventional non-retractable scalpel handles.

U.S. Pat. No. 5,527,329 (GHARIBIAN) discloses a surgical scalpel having a retractable sleeve; an elongated handle having a delimited grip portion is releasably connected to a blade holder supporting the surgical blade. The blade holder is secured to the handle by a hook and groove assembly and through a male-to-female engagement. The sleeve slides between an extended position and a backwards position on the handle and the blade holder. The extended position of the sleeve covers the blade safeguarding the user. An arch on the sleeve contacts the hook and disengages it out of the groove to facilitate removal of the blade holder.

U.S. Pat. No. 5,312,429 (NOACK) discloses an apparatus whereby a detachable surgical blade is easily and effectively removed from blade holder handle suitable for use with detachable surgical blades. The apparatus is a two part assembly comprising a scalpel handle and a removable sliding blade-shaped element. The handle includes a blade mounting tang on the proximal end thereof and a grip on the distal end thereof. The handle has sizes such that a portion of the rear edge of the scalpel blade protrudes latitudinally beyond the perimeter of that portion of the grip adjacent to the tang. The releasable sliding blade-shaped element is slidably mountable on the handle and it is of a length such that, when assembled with the handle, the releasable sliding blade-shaped element extends forward from an intermediate section of the grip to a section of the rear grip of the tang. The release sliding blade-shaped element has a blade engaging and release ramp which inclines from the proximal end of the handle to the distal end of the handle as the blade mounting portion of the tang extends upwardly. Removal of the blade is accomplished by a one handed digitally activated sliding movement of the release sliding blade-shaped element towards the proximal end of the handle, whereas the blade engaging and release ramp engages the protruding portion of the rear edge of the blade causing the rear portion of the blade to flex upwardly and slide forward off the tang.

From a close examination of the handles used in surgical or anatomic dissection techniques, six positions can be indicated:
- first position: the handle grasped as a pen with the cutting edge downwards;
- second position: the handle grasped as a pen with the cutting edge upwards;
- third position: the handle grasped as a knife with the cutting edge downwards;
- fourth position: the handle grasped as a knife with the cutting edge upwards;

fifth position: the handle grasped as a violin bow with the cutting edge downwards;

sixth position; the handle grasped as a violin bow with the cutting edge upwards.

Accomplishing the pen-like grip, the handle is held between the thumb, the forefinger and the middle finger having as a resting surface the first interdigital area; accomplishing the grip as a knife the handle is held between the thumb by one side and the middle finger, the ring finger and the little finger by the other side, whereas the forefinger, used with a soft pressure, presses on the dorsal face of the scalpel; accomplishing the grip as a violin bow, wherein all the five digits are used, the handle is held between the thumb by one side and the forefinger, the middle finger, the ring finger and the little finger by the other side; this grip is the most suitable for carrying out a groove turning the cutting edge of the blade upwards. All the described conventional grips involve the prevalently opened position of the hand and accordingly the handle has a mostly elongate shape. According to the new handle object of the present invention and to obtain different and more ergonomic positions of the grip, a close examination of the anatomy of the hand has been done. It has been examined the front face or palm, the rear face or dorsal, the medial edge, the lateral edge and the distal edge from which respectively the digits originate. Anatomically, the palm of the hand helps the grasping motion through the most developed protrusion corresponding to the base of the thumb constituted by the fleshy mass of three muscles, having ovoidal elongate shape with the larger portion towards the wrist; this protrusion works in combination with an other protrusion on the opposite side, less outstanding, having an elongate elliptical shape and corresponding to the little finger. The grip, according to the used handles, is directed by the different digits.

The skeleton of the hand has a slightly transversal convex shape and the spaces among the metacarpal bones are filled by the dorsal interosseous muscles and above the deep surface, the tendons of the extensor muscles of the digits run, which have a different length one from the others, the thumb 12 is shorter consisting of only two phalanxes, the middle finger 13 is the longest, the forefinger 11 and the ring finger 15 are generally of the same length and their tips arrive to the midway point of the terminal portion of the middle finger, whereas the little finger 17 ends at the high of the second interphalangic articulation of the ring finger 15.

The gripping movements of the hand on the scalpel are obtained, as well as from the combined action of the digits on it, through the balancing and guiding effect of the palm of the hand on the instrument, whereas the cutting, the incision and the scission actions of the set handle/blade are obtained through the combined action of the bending movements, extension movements, radial inclination movements, cubital inclination movements, as well as of circling movements and rotation movements of the hand according to the wrist; accomplishing the bending movement, the palmar face of the hand bends itself towards the medial surface of the forearm, whereas for the extension movement the dorsal face of the hand bends itself according the lateral surface of the forearm; accomplishing the cubital inclination movement, the hand bends itself towards the cubital side of the forearm and in the radial inclination movement the hand bends itself towards the radial side; the sequence and the combination of the above described movements cause the circling, whereas the radial rotation is obtained by the movement of the hand on its own axis. The described movements and the grasping motion used in the aforesaid three principal grips—such as a pen, as a knife and as a violin bow—are not certainly achievable through the handles of conventional scalpel, which are mainly rectilinear and elongated.

The first inconvenience is the limited grip surface and the impossibility to use correctly, in the grasping motion, the protrusion at the base of the thumb and the eminence at the base of the little finger, as well as the inconvenience of not use the palmar face in the extension and in the cubital inclination movements, which causes a weak and slightly perceivable cutting action of the scalpel.

The non-correspondence of conventional handles having an elongate bar to the anatomy of the hand causes that the cutting, incision and division motions are charged on the carpiradialis and carpiulnaris articulations which early cause stress disorders that surgeons well know.

Another inconvenience of conventional elongate handles has been observed through sophisticated studies of the working of the surgeon's hand; when he carries out through the scalpel a deep cutting motion, he is obliged to release the grip from the blade, moving his hand towards the tang of the handle. He can obtain the wanted purpose, but he has lesser control of the direction, pressure and precision of the cut.

BRIEF SUMMARY OF THE INVENTION

Aim of the present invention is to provide an anatomic handle for surgical precision scalpel to be effectively used for all the grips in surgical or anatomic dissection techniques, and which can be grasped as a pen with the cutting edge downwards and upwards, or as a knife with the cutting edge downwards and upwards, or as a violin bow with the cutting edge downwards and upwards.

Another aim is to provide a handle for surgical scalpel that is anatomically compatible with the osseous and muscular structure of the hand such as to allow a stable and highly accurate grip, advantageously and completely using the guiding action of the digits on the instrument, even without the balancing action of the palm of the hand and to obtain a cutting, an incision and division motion from the set handle/blade through the combination of the bending movements, extension movements, radial inclination movements, cubital inclination movements as well as circling and rotation of the hand according to the wrist.

Another aim is to provide an handle for scalpel wherein the surface of lateral grip is greatly larger than the handles of known scalpel and wherein the cutting motion of the instrument is felt by the user in whatever position he holds the scalpel.

Another aim is to provide a scalpel having the handle according to the invention, by means of which the surgeon obtains a control of the direction and precision of the cut, limiting at the most the inaccuracy of said actions due to stress or to the feeling of fatigue caused by a non-correct ergonomic grip; said aim can be also achieved even in case the surgeon has rough grips.

Another aim is to provide the maximum efficiency by using the scalpel, even in the case the surgeon is somehow encumbered in achieving precision movements of his digits, provided that this impediment is not an obstacle to the professional work of the same.

Last but not less important aim is to provide a handle for scalpel of absolutely simple manufacture, without movable or assembled parts, which can be manufactured through highly industrialized processes and at a low cost, to supply great quantities of the product.

These aims are achieved according to the invention by an anatomic handle for surgical precision scalpel comprising a first upper curved body corresponding anatomically to the curved shape of the forefinger in a gripping position as shown in FIG. 6, and longitudinally corresponding to the portion of the hand comprised between the tip of the forefinger and the hollow connecting the forefinger itself to the thumb. Said first body is connected to a second underlying body as a prosecution of the first one, having an asymmetric overturned-saddle shape obtained through a first front gorge turned towards the external jointed to a second rear gorge also turned towards the external but according to an opposite direction by means of an inverted curve, said first and second gorges having a specific ergonomic purpose for the grip; said handle having furthermore a central lightened area determined by the combination between the first upper body and the second underlying body, having the same shape but a smaller size than the whole shape of said handle, said shape may be hollow; said handle being effectively used as a scalpel through two equal and opposite heads placed at the two terminal portions of the first curved body constituting on the upper part an ergonomic tang, said first front head fit for housing on its dorsal face the tip of the forefinger of the hand, said second rear head fit for resting on the hollow connecting the base of the forefinger to the base of the thumb, said first and second heads presenting each on the lateral face the connection for an interchangeable blade, said blade placed horizontally according to the cutting plane.

BRIEF DESCRIPTION OF THE SEVERAL VIEWS OF THE DRAWINGS

For a better understanding of the present invention it is described hereinafter a preferred embodiment, only by way of example and not of limitation, according to the attached drawings FIG. 1 is a side elevation view of the first lateral face of the handle.

FIG. 2 is an opposite side elevation view of the second lateral face of the handle.

FIG. 3 is a top plan view from above with a transversal schematic section, according to axis A-A'indicated in FIG. 1.

FIG. 4 shows art a cross-sectional view of a usual section of the main curved body of the handle.

FIG. 5 is a detailed side elevation view of a blade to be applied to the heads of the handle.

DETAILED DESCRIPTION OF THE INVENTION

Figure 7:
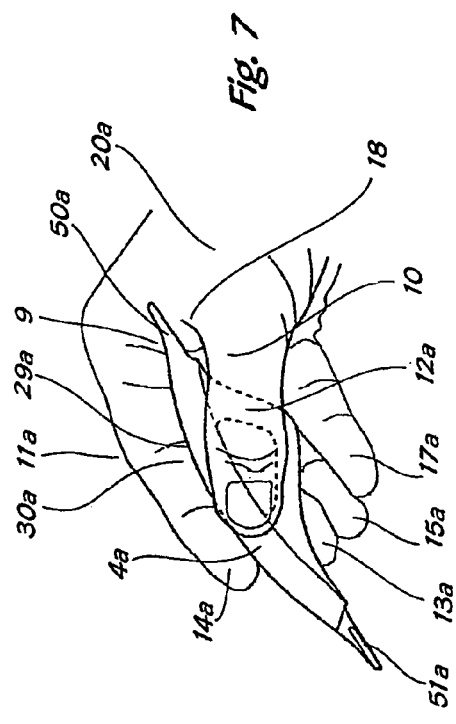
FIG. 7 shows another Perspective view of the scalpel used in a second grip.

As shown in FIGS. 1-4, an anatomic handle for surgical precision scalpel has a first upper body 4 constituted by a curved little bar 6 whose conventional transversal section 25 has an approximately trapezoidal shape with the larger base 24 slightly rounded and turned upwards, jointed through two bevels 26 and 26a to the respective lateral faces 27 and 27a having a slightly concave shape; the longitudinal length of said body 4 is approximately equal to the portion of the hand comprised between the tip of the forefinger 11 and the hollow 18 connecting the base 9 of the same forefinger with the base 10 of the thumb 12, from such shape two heads 50 and 51 are projecting.

Beneath and as a prosecution of the first body 4, a second body 5 develops from the smaller base 28, said second body is constituted by a ribbon-shaped plate having a rectangular and very flatten section 23 and having a longitudinal length corresponding to the first body 4, connected to said first body through two terminal portions whose asymmetric overturned-saddle shape 31 is obtained by a first front gorge 32 turned towards the external and by a second rear gorge 33 longitudinally larger than the first one and turned towards the external but in an opposite direction than the first one, said two gorges jointed through an inverted curve 34, said first and second gorges having an ergonomic specific purpose among the range of different possible grips. The combination of the first body 4 curved upwards with the second body 5 which is mainly extended downwards carries out a central hollow area 7, whose shape is morphologically determined by the connection between the first upper body 4 and the second underlying body 5, said area 7 accordingly maintains the same shape of the whole set of said handle, but it has a smaller size and has a first front curve 132 and a second rear curve 133, connected each other through an inverted curve 134; in such hollow area 7, the thumb inserts itself whatever grip is accomplished and consequently the scalpel is more stable in the surgeon's hand compared to any conventional scalpel usually used.

As a prosecution of the body 4, respectively at its front terminal part and at its rear terminal part, there are the two heads 50 and 51, equal in their shape but opposite directed, so that the first front head 50 is directed towards the face 27 of the body 4, whereas the second rear head is directed towards the face 27a; said heads having each on the lateral side a joint, respectively 52 and 53, for an interchangeable blade 41, said blade through its shaped slot 40 is assembled horizontally according to the cutting plane.

Said two equal but opposite heads 50 and 51 constitute on the upper part an ergonomic tang, said first front head 50 fit for housing on the dorsal face the tip of the forefinger 11 of the hand, the second rear head 51 fit for steady housing itself into the hollow 18 connecting the base 9 of the forefinger 11 with the base 10 of the thumb 12.

Figure 6:
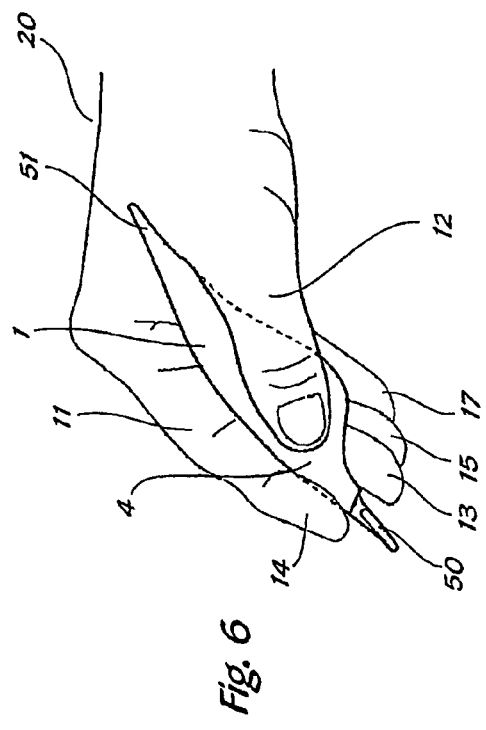
FIG. 6 shows a perspective view of the scalpel used in a first grip.

FIG. 6 shows an hand 20 that grasps a scalpel 1 as a knife, with the front portion (which is shorter) turned forward and with the blade turned downwards—that is to say with the handle held between the thumb 12 and the forefinger 11—whereas the middle finger 13, the ring finger 15 and the little finger 17 are rearwardly positioned; in such gripping position the tip 14 of said forefinger is positioned and therefore pushes in an area corresponding to the front terminal part of the body 4, where the front head 50 originates, in such a way to allow a limited cutting depth and a greater precision in micro movements.

FIG. 7 shows an hand 20a that grasps a scalpel 1a as a pen, with the front part (which is shorter) turned rearwardly and with the rear head having the blade turned downwards—even in this embodiment the handle is held between the thumb 12a and the forefinger 11a—and with the middle finger 13a, the ring finger 15a and the little finger 17a positioned rearwardly; the forefinger, which is superposed on its dorsal face on the upper body 4a of the scalpel and follows its upper curvature 29a—which anatomically corresponds to the longitudinal convexity 30a of an opened hand determines the right direction and course of the scalpel and proportions the cutting pressure. Said grip provides that the tip 14a of the forefinger 11a is placed back according to the head 51a holding the blade, in order to allow a larger cutting depth.

Figure 8:
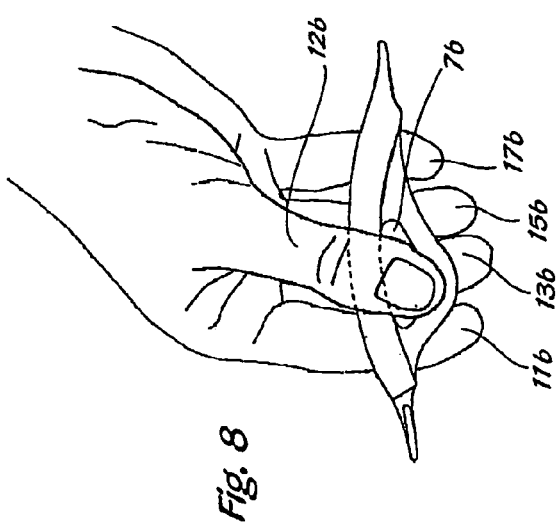
FIG. 8 shows another perspective view of the scalpel used in the violin bow-like grip.

FIG. 8 shows a violin bow-like grip position, wherein the thumb 12b is placed forward on the hollow area 7b whereas the other digits of the hand 11b, 113b, 15b, 17b, rearwardly opposite to it, determine the grip.

Figure 9:
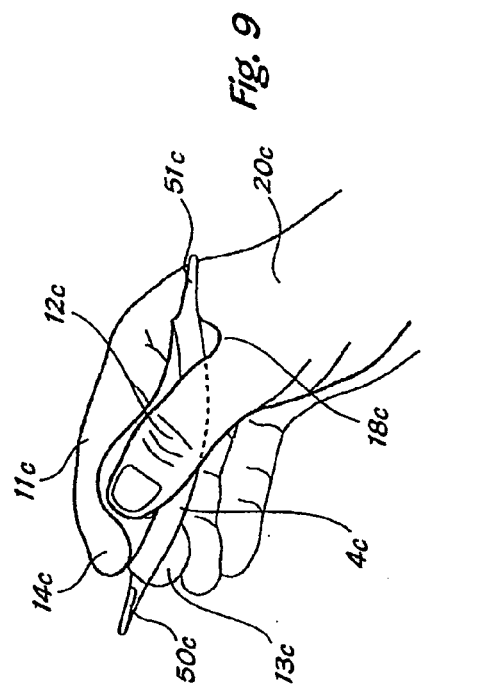
FIG. 9 shows another perspective view of the scalpel grasped with the blade upwards.

FIG. 9 shows a second pen-like grip, wherein the body 4c is turned downwards with the head 51c housed in the hollow 18c of the hand 20c and with the front head 50c turned upwards, in a guiding grip between the thumb 12c, the tip 14c of the forefinger 11c, guided and supported by the middle finger 14c.

It is evident that in all the above described and shown embodiments, as well as in all the other possible grip positions, the hollow area 7 of the handle is very important, because it allows a stable grip, facilitates the guidance and orientation of the scalpel and allows a great precision and accuracy in macro and micro movements of the hand.

I claim:

1. An anatomic handle for surgical precision scalpel comprising:
   a first upper curved body corresponding anatomically to a curved shape of a forefinger accomplishing a grasping position and as to its size longitudinally corresponding to a portion of a hand comprised between a tip of the forefinger and a hollow connecting said forefinger to a thumb;
   a second underlying body as a prosecution of said first upper curved body having an asymmetric overturned-saddle shape obtained through a first front gorge turned towards an external joint to a second rear gorge also turned towards the external joint but having an opposite direction by means of an inverted curve, said first and second gorges having a specific ergonomic purpose for the grip;
   a central lightened area determined by combination between the first upper body and the second underlying body, having the same shape but a smaller size than the whole shape of said handle, said shape may be hollow; and
   two equal and opposite heads placed at the two terminal portions of the first curved body having, on the upper part an ergonomic tang, said first front head fit for housing on the dorsal face the tip of the forefinger of the hand, said second rear head fit for resting on the hollow-connecting the base of the forefinger with the base of the thumb, said first and second heads presenting each on the lateral face the joint for an interchangeable blade, said blade horizontally positioned according to the cutting plane.

2. Anatomic handle for surgical precision scalpel according to claim 1, wherein said upper body is comprised of a little bar having a conventional transversal section of trapezoidal shape.

3. Anatomic handle for surgical precision scalpel according to claim 2, characterized by the fact that said shape has the larger base rounded and turned upwards.

4. Anatomic handle for surgical precision scalpel according to claim 3, characterized by the fact that said little bar has two lateral concave faces.

5. Anatomic handle for surgical precision scalpel according to claim 1, wherein said second body is comprised of a ribbon-shaped plate having a rectangular Section.

6. Anatomic handle for surgical precision scalpel according to claim 5, characterized by the fact that said ribbon-shaped plate has a very flatten section.

7. Anatomic handle for surgical precision scalpel according to claim 5, characterized by the fact that-said second ribbon-shaped body has a longitudinal size corresponding to said first body.

8. Anatomic handle for surgical precision scalpel according to the first claim, characterized by the fact that said second body underlying to the first one has a first front curved portion and a second rear portion also curved, said second portion having a longitudinally larger curvature.

9. Anatomic handle for surgical precision scalpel according to claim 8, characterized by the fact that said first and second curves are orientated according to an inverted direction.

10. Anatomic handle for surgical precision scalpel according to claim 9, characterized by the fact that said first and second curves are connected through a third curve having an inverted direction.

11. Anatomic handle for surgical precision scalpel according to claim 8, characterized by the fact that said second body has a first front curve longitudinally less extended than said second rear curve, allowing a front grip position different from the rear grip position.

12. Anatomic handle for surgical precision scalpel according to claim 11, characterized by the fact that said first front grip position allows a grip proximal to the first cuffing head.

13. Anatomic handle for surgical precision scalpel according to claim 11, characterized by the fact that said second rear grip position allows a grip distal to the second cutting head.

14. Anatomic handle for surgical precision scalpel according to claim 1, wherein said hollow area is morphologically comprised of a combination of the first upper body with the second underlying body and that in such hollow area, in the grasping position, the thumb can insert itself in said hollow area whatever the surgical grip is.

15. Anatomic handle for surgical precision scalpel according to the first claim, characterized by the fact that said heads have on their lateral face a joint for an interchangeable blade.

16. Anatomic handle for surgical precision scalpel according to claim 15, characterized by the fact that said interchangeable blade is assembled on the joint placed on the head through a shaped slot of the same blade.

17. Anatomic handle for surgical precision scalpel according claim 1, wherein said handle, during surgical maneuvers, can be grasped as a knife, with the first front head in working position, with the blade turned downwards and the handle between the thumb and the forefinger, whereas the second head balances the lever working in the hollow connecting said forefinger to said thumb.

18. Anatomic handle for surgical precision scalpel according to claim 1, wherein said handle in the surgical maneuvers can be grasped as a pen, with the first front head turned rearwardly, whereas the second head works forward with the blade turned downwards and the handle is held between the thumb and the forefinger.

19. Anatomic handle for surgical precision scalpel according to claim 1, wherein said handle in the surgical maneuvers can be grasped as a violin bow with the thumb inserted on the hollow area opposite to the other four digits.

20. Anatomic handle for surgical precision scalpel according to claim 1, wherein said handle in the surgical action can be gasped in a second pen-like grip motion, with the blade of the first front head turned upwards, whereas the second head works rearwardly in the hollow connecting said forefinger to said thumb, said grip being directional between the thumb and the tip of the forefinger, guided and supported by the middle finger.

* * * * *